United States Patent [19]

Metzler et al.

[11] Patent Number: 5,112,019
[45] Date of Patent: May 12, 1992

[54] MOTORIZED IV POLE ASSEMBLY

[75] Inventors: Michael E. Metzler, Webster Groves; Michael S. Ameiss, O'Fallon; James P. Baum, Defiance, all of Mo.

[73] Assignee: Storz Instrument Company, St. Louis, Mo.

[21] Appl. No.: 705,818

[22] Filed: Feb. 4, 1991

[51] Int. Cl.⁵ .................. A61M 5/00; A47G 29/00
[52] U.S. Cl. ........................... 248/405; 248/125; 248/176; 248/333; 248/550; 604/246; 604/65
[58] Field of Search ............... 248/125, 405, 161, 176, 248/188.5, 163.1, 332, 333, 550, 542; 604/65, 246; 128/DIG. 12, DIG. 13

[56] References Cited

U.S. PATENT DOCUMENTS

| | | | |
|---|---|---|---|
| 2,983,474 | 5/1961 | Hanna | 248/161 |
| 3,242,924 | 3/1966 | Kraft et al. | 128/DIG. 13 |
| 3,822,051 | 7/1974 | Karapita | 248/333 |
| 3,884,228 | 5/1975 | Hahn | 604/245 |
| 3,887,155 | 6/1975 | Bertalot | 248/333 |
| 4,475,668 | 10/1984 | Kawakami | 604/65 |
| 4,635,492 | 1/1987 | Uebelhart | 248/405 |
| 4,738,369 | 4/1988 | Desjardins | 248/333 |
| 4,744,536 | 5/1988 | Bancalari | 248/125 |
| 4,901,339 | 2/1990 | Heinz | 248/332 |

FOREIGN PATENT DOCUMENTS 13843 9/1887 United Kingdom ................ 604/257

Primary Examiner—Reinaldo P. Machado
Attorney, Agent, or Firm—Brooks & Kushman

[57] ABSTRACT

A motorized IV pole system for controlling the height of an IV container to thereby control the infusion pressure in an IV tube includes a telescoping IV pole system. In one embodiment, comprising three concentric support members, the outer support member is fixed, the middle support member is reciprocable with respect to the outer support member and is driven by a rack gear attached thereto. An inner support member is reciprocatable in the interior of the middle support member and is driven by a cable attached to the outer support member passing over a pulley attached to the middle support member. The rack on the middle support member may be driven by a shaft to which is attached a hand crank and an AC motor. The AC motor may be driven by a programmable control system which includes an optical encoder to permit display of the height of the IV container. Also, preselected heights and various speeds of height adjustment may be utilized. Another embodiment employs a tubular support member carrying a nut driven by a concentric threaded shaft. A friction-adjustable bearing for maintaining the position of the shaft permits manual height adjustment.

30 Claims, 7 Drawing Sheets

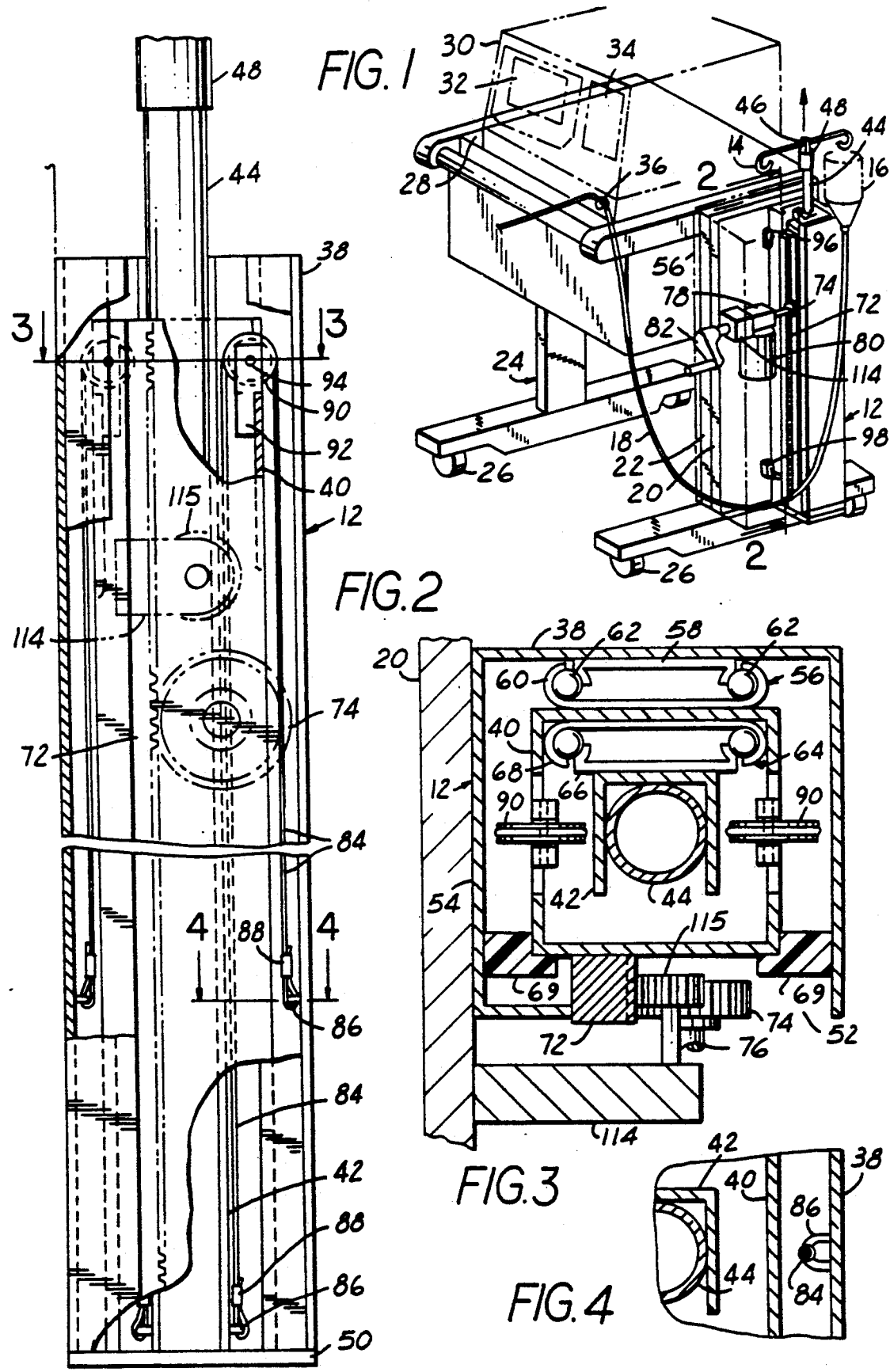

MOTORIZED IV POLE ASSEMBLY

CROSS-REFERENCE TO RELATED APPLICATIONS

The present invention is related to the subject matter of the following commonly assigned applications being filed and incorporated by reference:

Application Ser. No. 427,614 filed Oct. 27, 1989, entitled "Remote Control Console for Surgical Control System";

Application Ser. No. 428,355 filed Oct. 27, 1989, entitled "Footswitch Assembly with Electrically Engaged Detents";

Application Ser. No. 428,166 filed Oct. 27, 1989, entitled "Motorized IV Pole Assembly"; and Application Ser. No. 438,863 filed Nov. 20, 1989 entitled "Control System for Ophthalmic Surgical Instruments" which is a Division of Ser. No. 267,713 filed Nov. 4, 1988 and is now U.S. Pat. No. 4,933,843 issued Jun. 12, 1990 which is a continuation of Ser. No. 928,170 filed Nov. 6, 1986, now abandoned.

FIELD OF THE INVENTION

The present invention relates in general to parenteral liquid container support devices, and, in particular, to apparatus and systems for controlling the height of such containers.

DESCRIPTION OF RELATED ART

The infusion of parenteral, or intravenous, liquids is a pervasive technique in hospitals and other health care settings. Intravenous ("IV") liquid containers typically comprise flexible or rigid vessels suspended in an inverted position with an IV tube extending downward from the IV container opening. The other end of the IV tube is then attached to the patient in the appropriate manner for infusion of the IV fluid.

The intravenous container is typically suspended from a hanger attached to an IV pole. While IV pumps are sometimes used, normally the height of the IV container provides the necessary fluid pressure, or head, to infuse the IV fluid into the patient. In many circumstances, for example, during ophthalmic surgery, it is desirable to replace intraocular fluids which are removed during the surgical operation. Typically, during such surgery, an IV apparatus with an adjustable pole is used to infuse fluids, such as physiologic saline, through a cannula inserted into the eye. In this manner, the pressure in the eye stabilizes at a point determined by the physical elevation of the saline column above the level of the eye. This physical elevation is typically adjusted by manually raising and lowering the IV pole. For example, such poles are frequently fitted with a telescoping adjustment mechanism that permits manually raising and lowering the IV pole to a desired height.

Manual adjustment of the height of the IV pole, however, has a number of disadvantages. The process of loosening, raising and retightening the IV pole is time-consuming and distracts operating room personnel from other important functions. Also, manual adjustment of the IV pole height is slow and carries with it inherent inaccuracies, which effect the resulting infusion pressure. Further, during manual adjustment, there is the possibility of the pole accidentally slipping and thus permitting the IV pole to lower, reducing the infusion pressure to undesirable low levels temporarily.

Thus, it would be very desirable to have an improved system for quickly and accurately raising and lowering the height of an IV pole to a predetermined level.

In light of the foregoing problems and desires, it is a primary object of the present invention to provide an IV pole in which the height is easily and quickly adjusted.

One more object of the present invention is to provide an IV pole in which the height may be adjusted automatically without manual effort; for example, by merely pushing a button.

Still another object of the present invention is to provide an IV pole in which the height of the IV container is displayed to thereby facilitate adjusting the height to a desired level.

It is another object of the present invention to provide a programmable system for controlling the height of an IV pole in which the pole may be automatically adjusted to a preprogrammed height.

SUMMARY OF THE INVENTION

In light of the foregoing desires and objects, there is provided, in accordance with the present invention, a system for adjusting the height of an IV pole apparatus. The IV pole system, in accordance with the first embodiment of the present invention, includes a hanger for supporting a parenteral, or intravenous, liquid container and a vertically telescoping support apparatus for changing the height of the hanger. The telescoping support apparatus includes concentric outer, middle and inner elongated support members, the hanger being attached to the upper end of the inner support member. The middle support member has a pulley attached near its upper end and a cable with a first end attached to the lower end of the inner support member. The cable has its second end attached to the outer support member. The cable is disposed so as to engage with the pulley. A drive means is coupled to the middle support member for moving vertically the middle support member. As a result, vertical motion of the middle support member is transmitted through the cable to the inner support member.

To maintain the inner and middle elongated support members disposed in a relatively vertical position, a guide is provided for permitting reciprocating motion of the middle and inner support members with respect to the outer support member. A motor may be attached to the drive means to provide for automatically raising and lowering the IV pole assembly.

In accordance with a second embodiment of the present invention, an apparatus for controlling the height of a parenteral, or IV, liquid container is provided having a hanger for supporting the IV liquid container and a telescoping support for changing the height of the hanger that includes a plurality of concentric elongated support members. A drive means cooperates with the telescoping support member for reciprocating vertically the concentric elongated support members. An electronic controller controls the drive means and includes a circuit for activating the drive means in a first direction and also a circuit for activating the drive means in a first direction and also a circuit for activating the drive means in the opposite direction. The controller may include a circuit for changing the speed of the drive means as well as a sensor for sensing the height of the IV liquid container and a display for displaying the sensed height of the IV liquid container. In addition, a preselected height may be stored in the electronic controller and the drive means may be activated automatically until the preselected height is reached.

Another embodiment includes a threaded shaft engaging a nut secured to a displaceable support member. Preferably, the shaft is concentric with the support member and retained in an adjustable compression bearing. The friction force maintaining the position of the support member is easily overcome by manual force applied directly to the support member for emergency fluid flow changes. A separate sensor gauges the displaced position of the support member.

These and other aspects, objects, features and advantages of the present invention will be better understood by considering the detailed description below and the appended claims in conjunction with the drawings.

BRIEF DESCRIPTION OF THE DRAWINGS

In the accompanying figures, where like items and features are identified by identical reference numerals in the various figures:

FIG. 1 is a perspective view showing the IV pole system in accordance with the present invention mounted on a movable cart;

FIG. 2 is a fragmentary cross-sectional view taken along line 2—2 of FIG. 1 showing the telescoping IV pole assembly;

FIG. 3 is a cross-sectional view of the telescoping IV pole assembly taken along line 3—3 of FIG. 2;

FIG. 4 is a fragmentary cross-sectional view showing the cable attachment taken along line 4—4 in FIG. 2;

DETAILED DESCRIPTION OF THE PREFERRED EMBODIMENT

Figure 5:
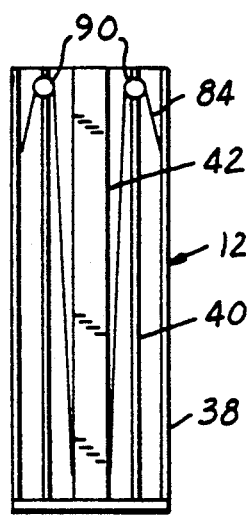
FIG. 5 is a diagrammatic side view of the IV pole assembly in the fully retracted position in accordance with the present invention.
Figure 6:
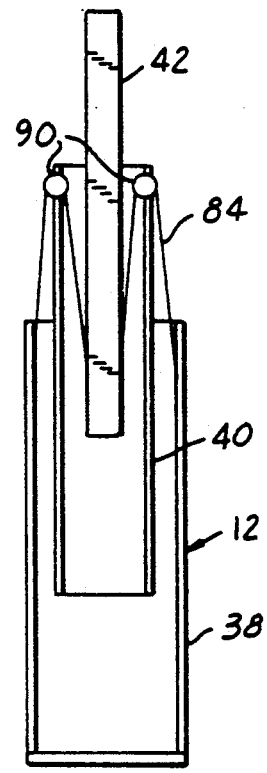
FIG. 6 is a diagrammatic side view of the IV pole assembly shown in FIG. 5 in a partially extended position.
Figure 7:
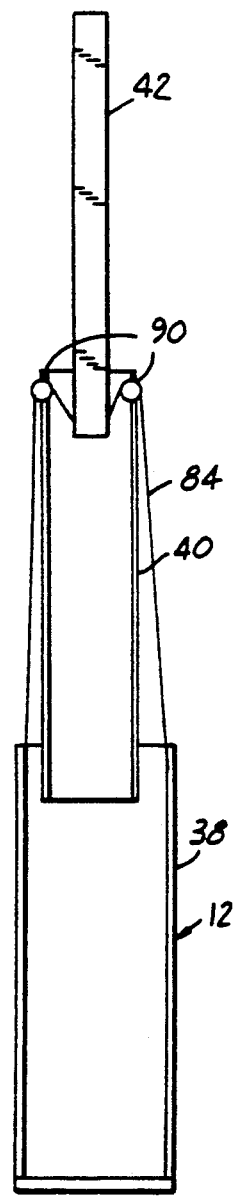
FIG. 7 is a diagrammatic view of the IV pole assembly shown in FIG. 5 in the fully extended position.

Referring now to FIG. 1, there is shown a motorized IV pole system 10 of the present invention which includes a telescoping IV pole assembly 12 upon which is attached a conventional IV container hanger 14. One or more IV containers 16 hang inverted from the IV hanger 14 in a conventional manner. Parenteral, or intravenous fluid, such as balanced salt solution, passes through an IV tube 18 to the patient (not shown).

The telescoping IV pole assembly 12 is bolted to a mounted plate 20 which is, in turn, bolted to cart mount 22 by means of conventional T-shape slots in cart mount 22 to permit easy removal of the telescoping IV pole assembly 12. The cart mount 22 is attached to a cart 24 which includes casters or wheels 26 to permit movement of the entire motorized IV pole assembly 10. The cart 24 includes a flat table 28 upon which is placed a control system 30 which includes a CRT 32, a motorized IV pole control panel 34, and an irrigation pinch valve 36. The IV tube 18 passes through the irrigation pinch valve 36 to provide a means for cutting off irrigation through the IV tube 18, when desired.

Turning now to the telescoping IV pole 12 as shown more clearly in FIGS. 2 through 7, the telescoping IV pole 12 includes three concentric support members, or channels, which are fabricated from square aluminum tubing. The outer support member 38 is manufactured from three inch square aluminum tubing, the middle support member 40 is manufactured from two inch square aluminum tubing, and the inner support member 42 is manufactured from one inch square aluminum tubing. A cylindrical tube 44 is inserted within, and attached to, the inner support member 42. An inner telescoping member 46 is inserted within the cylindrical tube 44 and is attached to the hanger 14. A rotatable tightening collar 48 permits the inner tube 46 to be extended to allow manual adjustment of the height of the IV container 16 if required. Cylindrical tube 44, inner telescoping member 46 and collar 48 are of the type commonly used, for example, in conventional IV stands and microphone stands.

The outer support member 38 includes a bottom plate 50 and a slot 52 in one of its sides. The inner wall 54 of the outer support member 38 is attached to the mounting plate 20, and the entire IV pole assembly 12 is enclosed by a rectangular enclosure 56 as shown in phantom in FIG. 1. The inner support member 40 is movable with respect to the outer support member 38 by means of a conventional drawer slide 56 which includes a first rail 58 that is attached to the outer support member 38, and a second rail 60 that is attached to the inner support member 40, as well as a series of ball bearings 62 which engage with rails 58 and 60 to permit relative telescoping motion between the two. Likewise, the inner support member 42 is permitted to move vertically with respect to the middle support member 40 by means of a second conventional drawer slide 64 which includes a first rail 66 attached to the inner support member 44, a second rail 68 attached to the middle support member 40 and a series of ball bearings 70 engaging with the first and second rail 66,68. A pair of guides 69 are located inside outer support member 38 to further restrict lateral motion of the middle support member 40. The guides are preferably made of nylon or a material which is relatively rigid but allows sliding movement thereon without significant friction.

To drive the middle support member 40 vertically, a rack gear 72 is attached to the middle support member 40 and extends from the bottom of the middle support member 40 to just past the drive gear 74. A drive or pinion gear 74 is attached to a shaft 76 to drive the rack 72. Shaft 76 extends from gear reduction unit 78 which is coupled to motor 80 and hand crank 82. Thus, pinion gear 74 may be driven by either hand crank 82 or electric motor 80 to raise or lower the middle support member 40. Motor 80 is a conventional two speed, reversible AC right angle gear motor that generates about 60 inch-pounds of torque at both 66 revolutions per minute and at 33 revolutions per minute. Gear reduction unit 78 serves to reduce the input rpm from the motor 80 to the shaft 76. Gear reduction unit 78 also serves to translate the vertical rotational axis of the motor 80 to a horizontal rotational axis of an output shaft 76. Control over the operation of the motor 80 is achieved by means of the control system 30 as will be explained in more detail below.

The telescoping IV pole 12 operates as follows. When shaft 76 rotates, pinion gear 74 will drive rack gear 72 to raise or lower the middle support member 40, which will be guided on drawer slide 56 with respect to the outer support member 38. As middle support member 40 raises or lowers, inner support members 42 will also be caused to raise or lower, as illustrated diagrammatically in FIGS. 5-7. Motion of middle support member 40 is coupled to that of the inner support member 42 by means of cable 84, one end of which is coupled to the inner wall of outer support member 38. A tie-down 86 is attached to the inner wall of support member 38 and one end of cable 84 is looped through tie-down 86 with the end of cable 84 crimped to an adjacent portion of cable 84 using a conventional crimp 88. A pulley 90 is located at the upper edge of middle support member 40 by means of a bracket 92 to permit pulley 90 to rotate about axis 94. Cable 84 extends upward from tie-down 86 in the interior of support member 38 and is looped around pulley 90 to extend back down in the interior of support member 40 to the lower portion of inner support member 42 where it is attached to inner support member 42 by means of a second cable tie-down 86 and crimp 88. It can be seen in FIGS. 5-7, coupled in this manner by means of cable 84, when middle support member 40 is raised a given distance with respect to outer support member 38, inner support member 42 will be raised twice that distance with respect to outer support member 38. It can also be seen that this motion of inner support member 42 may be achieved with a single cable 84 and pulley 90. However, as shown in FIGS. 1-7, a second cable 84 and pulley 90 is utilized to provide more even distribution of forces and also to provide a backup in case of failure of one of the cables 84. It will be appreciated that during lowering of inner support member 42, the weight of the lower support member, complete with the low friction required to operated slides 56,64, will allow cable 84 to remain taut throughout the down operation. Thus, inner member 42 is not driven down but is permitted to slide down under its own weight.

In order to limit the travel of the middle and inner support members 40 and 42, limit switches 96 and 98 are provided. Limit switch 96 is mounted externally at the upper end of outer support member 38 and limit switch 98 is located in the lower external side of outer support member 38. A cam (not shown) protruding from middle support member 40 is positioned so as to engage and trip limit switch 96 when middle support member 40 reaches an acceptable upper limit of travel. Likewise, limit switch 98 is positioned so that the cam (not shown) on middle support member 40 trips limit switch 98 when middle support member 40 has almost reached the lower acceptable limit of travel. Limit switches 96 and 98 may then be coupled to electric motor 80, for example, through control system 30 to de-energize motor 80 when either limit switch 96,98 is tripped. In this way, motion of the middle support member 40 is limited to with desired upper and lower limits. For example, it may be desirable to limit travel so that a minimum of 25% overlap between adjacent support members is maintained.

Figure 8:
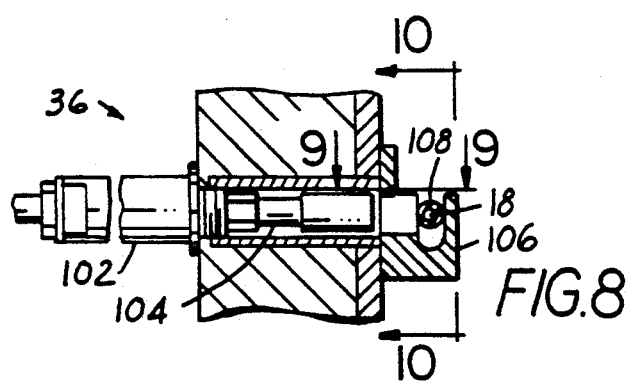
FIG. 8 is a cross-sectional view of the IV tube pinch valve mechanism in accordance with the present invention.
Figure 9:
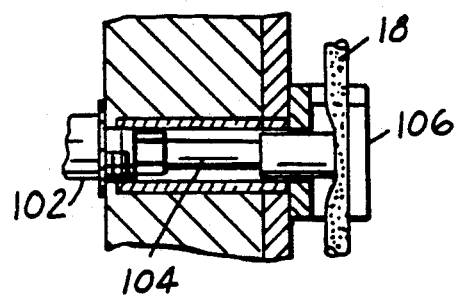
FIG. 9 is a cross-sectional front view of the IV tube pinch valve, mechanism taken along line 9—9 in FIG. 8.
Figure 10:
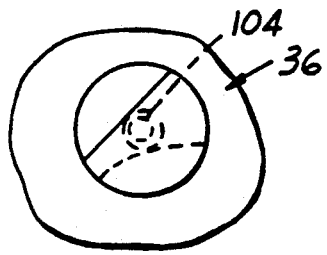
FIG. 10 is a cross-sectional view of the IV tube pinch valve mechanism taken along line 10—10 in FIG. 8.

Referring now to FIGS. 8-10, the irrigation pinch valve 36 is shown attached to the front panel 100 of the control system 30. Pinch valve 36 includes a solenoid 102 having an actuator 104 and an IV tube holder 106, having a channel 108. As shown in FIG. 8, an IV tube 18 rests snugly in channel 108. As seen in FIG. 9, when solenoid 102 is activated, actuator 104 will move into channel 108, pinching off IV tube 18 and preventing flow of fluid through tube 18. In order to prevent crimping and thus undesirable flow of IV fluids through the tube 18, the IV tube holder 106 has a rounded or preferably semi-circular shaped channel 108.

Figure 11:
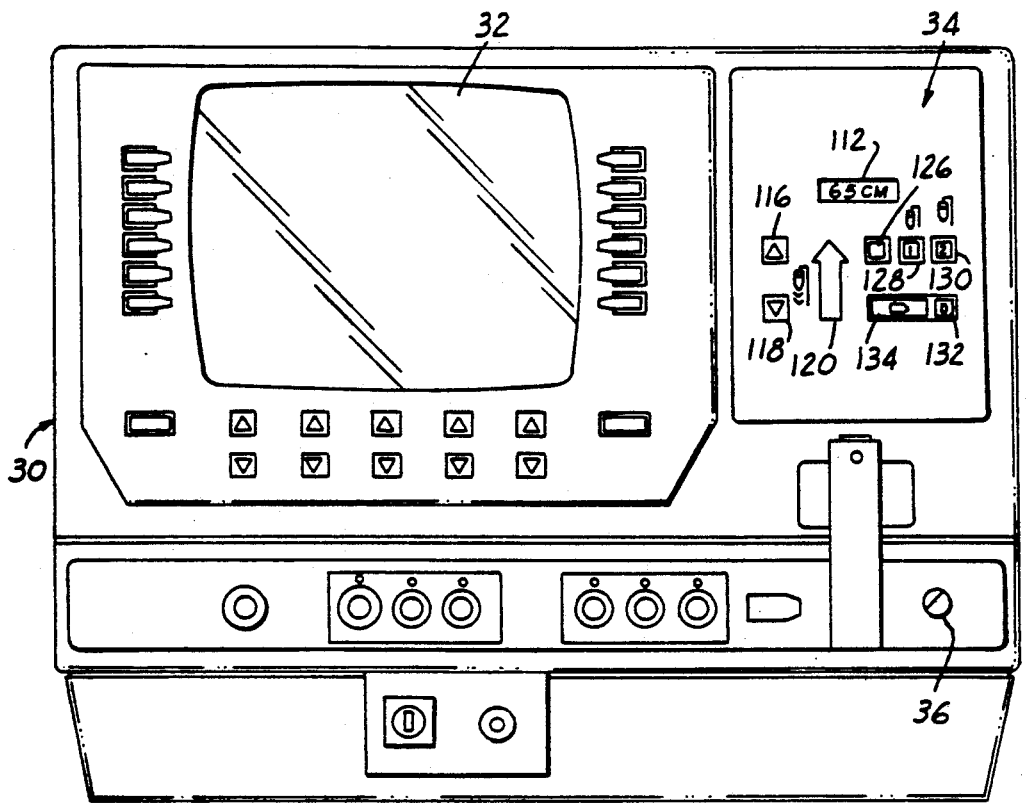
FIG. 11 is a plan view of an electronic controller console for the IV pole assembly in accordance with the present invention.

Referring now to FIG. 11, the control system 30 is shown. Control system 30 may be used to control other ophthalmic surgical instruments besides the motorized IV pole, as described in commonly assigned patent application Ser. No. 438,863 entitled "Control System for Ophthalmic Surgical Instruments," which was incorporated by reference above. Control over the IV pole height is achieved by means of an IV control keyboard 34 which includes an IV pole height indicator 112, which displays, in centimeters, the height of the IV fluid container 16 with respect to the patient.

The displayed height may be calculated by means of an optical encoder 114, as shown in FIGS. 2 and 3, which includes a gear 115 that is driven by rack 72. Optical encoder 114 may be a quadrature type encoder which is capable of detecting the amount, as well as direction, of rotation of shaft 76, as will be appreciated by those skilled in the art. Optical encoder 114 will be able to provide a resolution such that pole height indicator 112 will typically have an accuracy of + or −1.0 centimeter.

Figure 12:
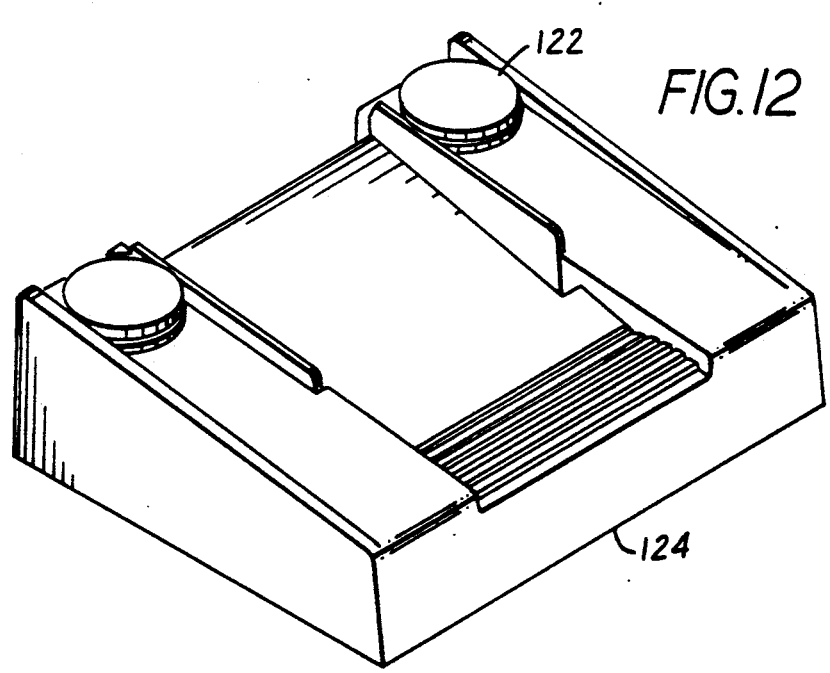
FIG. 12 is a perspective view of a foot switch for controlling the IV pole assembly in accordance with the present invention.

Control panel 34 also includes a UP key 116 which will activate motor 80 to move the IV container 16 up at a slow rate, while the key is held, until the container 16 reaches the upper limit, as indicated by the activation of upper limit switch 96. Likewise, DOWN key 118 will move the IV container 16 downward at a slow rate while key 118 is held, until the lower limit is reached as indicated by actuation of the lower limit switch 98. RAPID UP key 120 will move the IV container 16 up at a fast rate while the key is depressed until the upper limit is reached. Alternatively, as shown in FIG. 12, foot switch 122, attached to a foot controller assembly 124, may be used in lieu of RAPID UP switch. Further details of the foot controller assembly 124 and its operation are described in commonly assigned application Ser. No. 428,355 entitled "Foot Switch Assembly with Electrically Engaged Detents," which was incorporated by reference above.

Also, on IV control panel 34 is a set switch 126 which is used to establish preset heights for the IV pole 12. In particular, the set switch 126 places the IV controller 30 in a position storage mode. The IV display 112 blinks, showing the IV bottle position until presets are pressed. These presets include: preset one 130, preset two 128 and the zero preset 132. In the position storage mode, pressing one of the presets will store the current bottle storage position in nonvolatile memory for future use. Presets one 128, and two 130, once set in the storage mode, may be pressed with a single touch which will move the IV bottle 16 to the preset storage position at a slow rate. A single touch of the UP 116, DOWN 118, or RAPID UP 120 buttons will cancel or override the preset operation.

The zero button 132 is also set in the storage mode as described above. Once this zero reference is established, the bottle is automatically moved to the preset zero level when button 132 is pressed. Movements lower than the bottle zero set level are displayed as a negative displacement. For example, negative displacement may correspond to a level below a balanced irrigation system, or negative infusion pressure.

Change bottle button 134, when depressed, will lower the IV bottle 16 to a convenient height to facilitate changing the bottle. In particular, upon pressing the change bottle button 134, the display 112 goes to "- - - ," and the current bottle position is stored as a temporary preset. The IV pole may now be repositioned using UP 116, DOWN 118, OR RAPID UP 120 keys to facilitate bottle changeover. A second press of change bottle key 134 will return the IV pole to the original position.

It should be noted that the control panel 34 may be located remotely from the controller 30, as described in more detail in commonly assigned application Ser. No. 427,614 entitled "Remote Control Console for Surgical Control System," which was incorporated by reference above.

Upon power loss, the controller 30 will maintain the current bottle position. However, manual adjustment, by means of crank 82, is still possible. Also, due to friction collar 48, it is possible to manually change the height of the IV pole in the event of a system malfunction.

Figure 13:
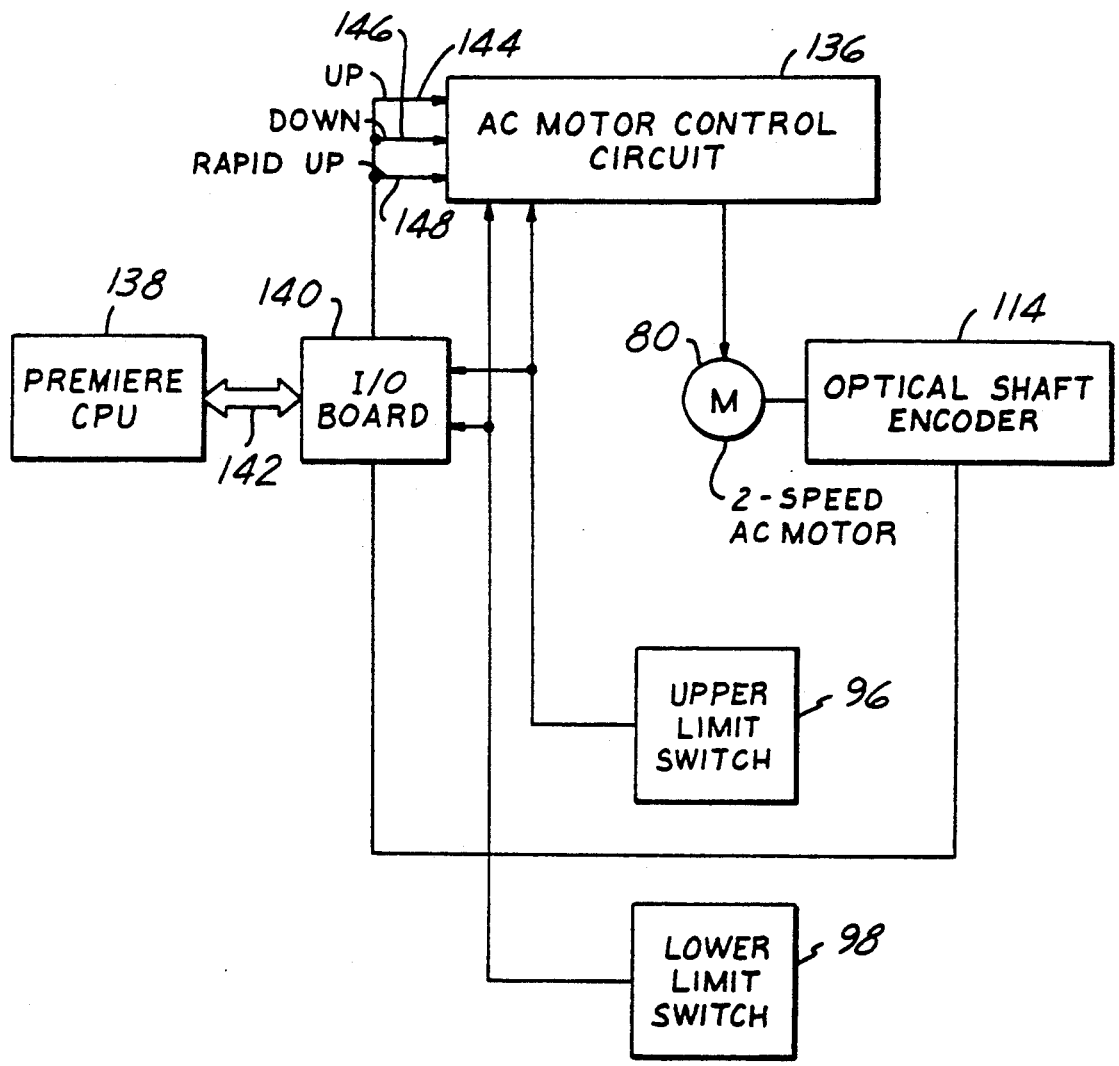
FIG. 13 is a block diagram of the motor control circuit of the IV pole assembly in accordance with the present invention.

Referring now to FIG. 13, there is shown a block diagram illustrating the electrical connections between the various components of the motorized IV pole system 10. The AC motor 80 is controlled by an AC motor control circuit 136. Signals from the IV control board 34 are directed to a CPU 138 in the control system 30 which is coupled to an I/O board 140 through a parallel communication bus 142 which may comprise a VME bus. UP 144, DOWN 146, and RAPID UP 148 lines from the I/O board 140, carry SIGNALS activated by the UP 116, DOWN 188, and RAPID UP 120 buttons, respectively, to direct AC motor control circuit 136 to drive motor 80 in the desired manner. Optical shaft encoder 114 transmits a signal to the I/O board 140 where it is available to the CPU 138 for processing to determine IV pole position. In addition, upper limit switch 96 and lower limit switch 98 are coupled to both the I/O board 140 and the AC motor control circuit 136 so that when one of the limit switches 96,98 is engaged, the motor 80 may be turned off automatically to prevent overtravel.

Figures 14, 15:
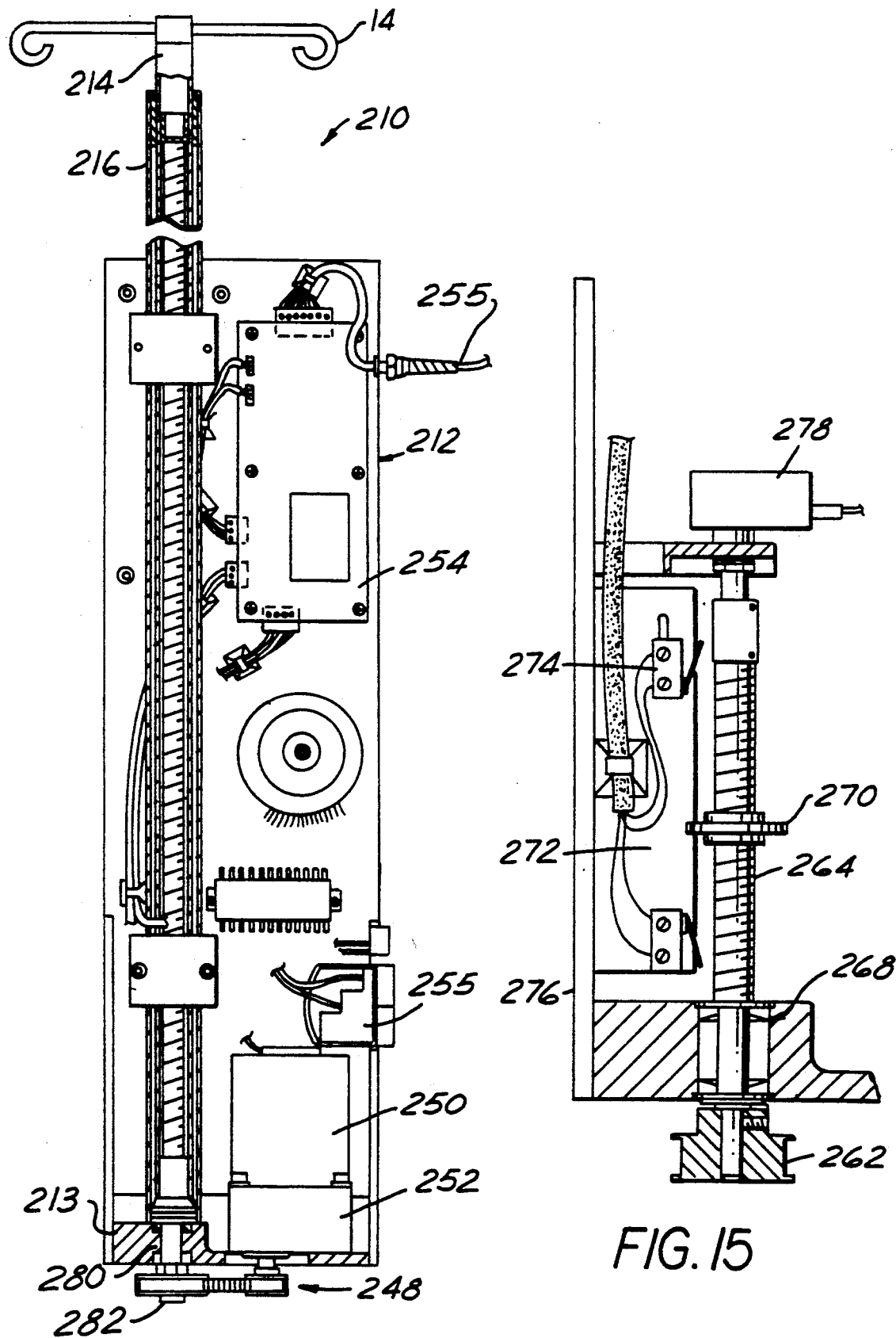
FIG. 14 is a side elevational view of a further preferred embodiment of the IV pole assembly constructed in accordance with the present invention, with the cover portion removed for the sake of clarity.
FIG. 15 is an enlarged elevational view of a sensor mechanism employed in the embodiment shown in FIG. 14.

Referring now to FIG. 14, a further embodiment of the motorized IV pole system 210 is thereshown carried in a housing 212. As shown in FIG. 14, the cover of the housing has been removed to reveal details of the motorized IV pole assembly 210. The container hanger 14 is carried by an inner support member 214 made of a cylindrical tube. The support member 214 is telescopically received in an outer support tube 216 which is supported upon the bottom plate 213 within the housing 212 and extends outwardly from the uppermost portion of the housing 212. The housing 212 is then coupled to a cart via connector 218. The connector 218 (FIG. 16) includes means for mechanically coupling the housing 212 to the cart as in the other embodiments.

Figure 17:
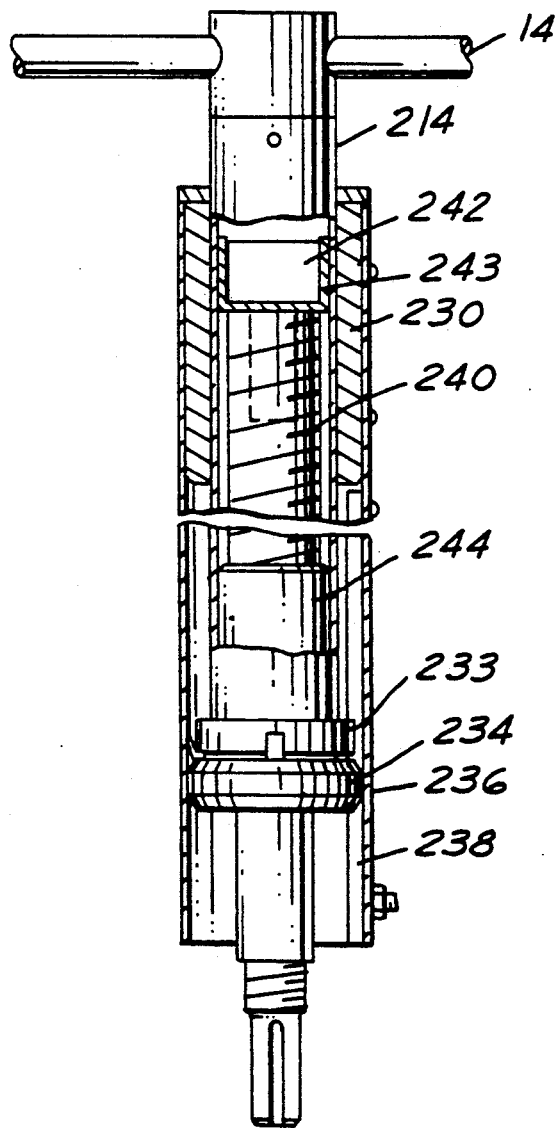
FIG. 17 is an enlarged, fragmentary sectional view of a portion of the apparatus shown in FIG. 14.

As best shown in FIG. 17, the support member 214 rides within a tubular sleeve 230 at the upper end of the outer support member 216. The tubular sleeve 230 is retained in the upper end of the outer support member 216 by screws. The lower end of the support member 214 slides onto the upper end of the drive nut 244. The support member 214 and drive nut 244 are affixed with flanges 233 and 234, respectively, on the lower end of each. Both flanges include a longitudinal notch at their outer edge adapted to receive an elongated rectangular guide bar 238 extending longitudinally along the inner wall of outer support member 216.

A threaded shaft 240 extends upwardly into the support member 214. Threaded shaft 240 has a cam follower 242 rotatably bolted to the shaft 240 at its upper end for support. The cam follower is received in a sleeve 243 which is rotatable therewith independently of both the support 214 and threaded shaft 240. Drive nut 244 threadably engages the shaft 240. As the threaded shaft 240 is turned, longitudinal notch in the flange 234 of drive nut 244 engages rectangular bar 238, translating rotational motion of threaded shaft 240 into vertical motion of drive nut 244 and support member 214. The lowermost end of the threaded shaft 240 extends outwardly from the support member 216 and the bottom plate 213 but within the housing 212 for engagement with a transmission 248.

Figure 18:
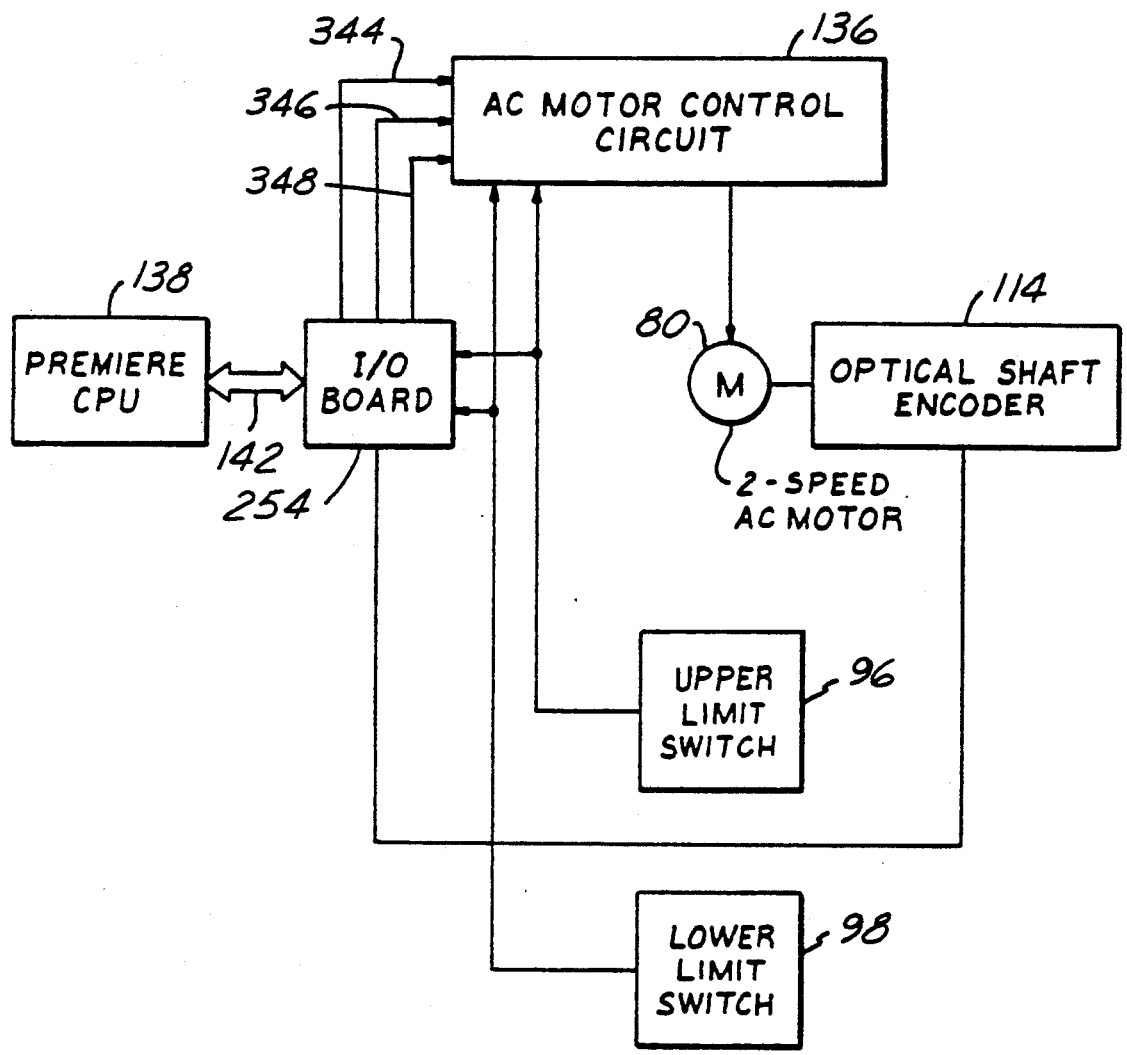
FIG. 18 is a block diagram similar to FIG. 13 but showing a circuit modification in accordance with the present invention.

Referring again to FIG. 14, the transmission 248 is coupled to a motor 250, such as an Oriental Motors 5IK 40 RGK-AA or 5IK 40 RGN-AUL variable speed motor, including a motor control pack 136 mounted to the control board 254, through a speed-reducing gear box 252. In the preferred embodiment, an Oriental Motors 5GK 6KA gear head having spur gears, or a 5GN 6KA gear head with helical gears, provides a 6:1 speed reduction ratio to drive shaft 256. Furthermore, the motor control is set up for two speed operation, i.e. RAPID UP is full motor speed, UP and DOWN keys operate motor 250 at half speed; by adjustment of the control pack. As shown in FIG. 18, the UP, DOWN and RAPID UP functions are actually a result of direction, speed and motor run/stop control signals 344, 346 and 348, respectively, applied to the motor control 136 from the control board 254. The motor is energized through a transformer power regulator from a pod 255 through the operation of the control pack. The power pod 255 has a three prong socket and provides a fused connection to an input power source. The power pod 255 also includes a tumbler for matching the voltage of standard U.S. and foreign power supplies.

Figure 16:
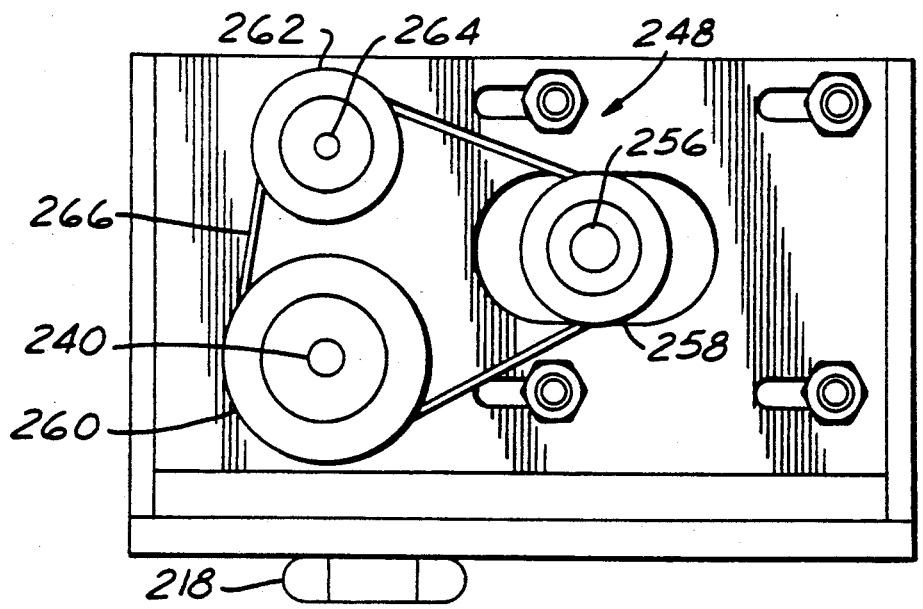
FIG. 16 is a bottom plan view of the IV pole assembly shown in FIGS. 14 and 15.

As best shown in FIG. 16, the transmission 248 includes the output shaft 256 from the gear box 252. A pulley 250 is mounted to the drive shaft 256. Similarly, a pulley 260 is mounted to the lowermost end of the threaded shaft 240. In addition, a pulley 262 is mounted to the sensor drive shaft 264. A belt 266 engages each of the pulleys 258, 260 and 262 so that the shafts 240 and 264 are driven at predetermined speeds as will be described in greater detail hereinafter. However, in the preferred embodiment, a 3:2 ratio is established between the pulley 260 and each of the pulleys 258 and 262.

Referring now to FIG. 15, the sensor shaft 264 extends through a bearing 268 mounted in the lower wall of the housing 212. The sensor drive shaft 264 has a threaded portion above the bearing 268 which carries a drive nut 270. Rotation of the drive nut 270 is restricted by a peripheral groove in the nut receiving an elongated guide bar 272. As a result, the periphery of the nut 270 is displaced between a pair of limit switches 274 and 276 electrically coupled to the control board 254. The distance between the switches 274 and 276 is a small fraction of the displacement of the support member 214 so as to reduce the size of the sensor mechanism. Nevertheless, the thread density of the threads on the shaft 264 and the speed at which the shaft 264 is rotated provides movement of the nut 270 proportional to the displacement of the support member 214 but within a substantially smaller space than required for limit switches which engage a cam on the support member 214.

In addition, the encoder 278 identifies rotational displacement of the shaft 264 to generate an input signal to the control board 254 for additional control of the support member 214 as in the change bottle preset condition described hereinafter.

As discussed above in relation to the sensor shaft 264, the threaded shaft 240 is also rotatably supported in a bearing 280 mounted in the lower wall of the housing 212. The bearing 280 is a compression bearing so that frictional resistance to displacement of the support member 214 can be adjusted. In the preferred embodiment, an angular contact bearing pair such as Barden Model 102 HDMG-6 bearings are inserted in upper and lower openings of the bottom plate 213. A nut 282 engaged on a threaded end portion of the shaft 240 can be tightened to axially compress the ends of the compression bearing 280 between the nut 282 and a step on the shaft 240. As a result, the tapered rollers of the compression bearing introduce radial forces creating additional frictional force against the shaft 240. This provides an adjustment of the resistance to movement that maintain the position of the support member 214 and the container once power has been removed from the motor 250. Nevertheless, it may be appreciated that the tension is also limited by adjustment of nut 282 so that the support member 214 can be manually extracted or retracted within the outer support member 216 by grasping the member 214 and manually retracting or extracting the member by merely overcoming the friction of the compression bearing 280 and the inertia of the transmission 248, gear box 252 and the motor 250.

On the other hand, when power is applied to the motor 250, and the control board 254 is coupled through cable 255 to appropriate control signals from the controller 30, support member 214, and thus the container carried by the hanger 14 can be raised and lowered as desired by operation of the switch controls on the controller 30. Moreover, activation of the change bottle preset switch enables a signal from the encoder 278 to be stored in memory. When the drive means is actuated to retract the support member 214 toward the bottom of the housing 212, the nut 270 approaches the lower limit switch 276 so as to interrupt power to the drive means, and maintain the hanger 14 at a low position, providing easy access for replacing the used container with a fresh bottle of parenteral fluid. When the replacement has been completed, the change preset actuator is again depressed to reenergize the drive means so as to displace the support member 214 vertically upward. Moreover, the encoder 278 again detects when the stored limit has been reached, and the drive means is deactivated so that the hanger 14 is repositioned at the level required by the surgeon conducting an ophthalmic operation.

Having thus described the present invention, many modifications thereto will become apparent to those skilled in the art to which it pertains without departing from the scope and spirit of the present invention as defined in the appended claims.

What is claimed is:

1. A system for supporting a parenteral liquid container comprising:
   hanger means for supporting said parenteral liquid container;
   vertical telescoping support means for changing the height of said hanger means, including concentric outer, middle, and inner elongated support members, said hanger means being attached to one end of said inner support member;
   said middle support member having a pulley attached near its upper end;
   cable means having a first end attached to the other end of said inner support member and having a second end attached to said outer support member, said cable means engaging with said pulley; and
   drive means coupled to said middle support member for moving vertically said middle support member wherein said vertical motion of said middle support member is transferred through said cable means to said inner support member.

2. The system according to claim 1 further comprising guide means for permitting reciprocating motion of said middle and inner support members with respect to said outer support member while maintaining said elongated support members disposed substantially vertically.

3. The system according to claim 1 further comprising a second pulley attached near the upper end of said middle support member opposite said first pulley, and a second cable means having a first end attached to the other end of said inner support member and having a second end attached to said outer support member, said second cable means engaging with said second pulley.

4. The system according to claim 1 wherein in said drive means further comprises a rotatable shaft having a pinion gear on one end, and a rack gear attached to said middle support member and engaged with said pinion gear, wherein rotation of said shaft is translated into vertical motion in said middle support member.

5. The system according to claim 4 wherein said drive means further comprises a hand crank for turning said rotatable shaft.

6. The system according to claim 4 wherein said drive means further comprises a motor engaged with said rotatable shaft for rotating said rotatable shaft.

7. The system according to claim 5 further comprising a programmable control means for controlling the height of said hanger means by energizing said motor in a predetermined direction and speed.

8. The system according to claim 6 further comprising a pair of sensors for detecting when said parenteral liquid container has reached predetermined upper and lower limits.

9. The system according to claim 1 wherein said outer, middle and inner elongated support members are generally square in cross-section.

10. An apparatus for controlling the height of a parenteral liquid container comprising:
   hanger means for supporting said parenteral liquid containers;
   telescoping support means for changing the height of said hanger means including a plurality of concentric elongated support members;
   drive means cooperating with said telescoping support means for reciprocating vertically said concentric elongated support members; and
   electronic controller for controlling said drive means including means for automatically actuating said drive means in a first direction to increase fluid pressure, and means for automatically actuating said drive means in a second direction to decrease fluid pressure.

11. The apparatus according to claim 10 further comprising means for changing the speed of said drive means.

12. The apparatus according to claim 11 further comprising means for sensing the height of said parenteral liquid container and means for displaying the height of said parenteral liquid container.

13. The apparatus according to claim 12 further comprising means for storing a preselected height of said parenteral liquid container and means for activating said drive means until said preselected height is reached.

14. The apparatus according to claim 12 wherein said means for sensing further comprises an optical encoder for sensing the position of said parenteral liquid container.

15. The apparatus according to claim 10 further comprising a pair of sensors for detecting when parenteral liquid container has reached predetermined upper and lower limits.

16. The apparatus according to claim 10 further comprising pinch valve means for cutting off the flow of liquid from said parenteral liquid container.

17. An apparatus for controlling the infusion pressure in an IV tube comprising:
   IV container for attachment to said IV tube;
   hanger means for supporting said IV container;
   vertical telescoping support means for changing the height of said hanger means including concentric outer, middle and inner elongated support members, said hanger means being attached to one end of said inner support member;
   said middle support member having a pulley attached near its upper end;
   cable means having a first end attached to the other end of said inner support member and having a second end attached to said outer support member, said cable means engaging with said pulley;
   drive means including a rotatable shaft having a pinion gear on one end, and a rack gear attached to said middle support member and engaged with said pinion gear, wherein rotation of said shaft is translated into vertical motion in said middle support member;
   electronic controller for controlling said drive means including means for actuating said drive means in a first direction, and means for actuating said drive means in a second direction; and
   means for sensing the height of said IV container, and means for displaying the height of said IV container.

18. The invention according to claim 10 wherein said first direction is vertically upward and said second direction is vertically downward.

19. Apparatus for controlling the pressure of a parenteral liquid container comprising:
   hanging means for supporting said parenteral liquid containers;
   telescoping support means for displacing the hanger means including a plurality of concentric elongated support members;
   drive means for longitudinally reciprocating at least one of said concentric support members; and
   an electronic controller for controlling said drive means including means for automatically actuating said drive means for displacing said at least one support member in a first direction to increase fluid pressure, and means for automatically actuating said drive means in a second direction for displacing said at least one support member to decrease fluid pressure.

20. The invention according to claim 19 wherein said first direction is vertically upward and said second direction is vertically downward.

21. The invention according to claim 19 and further comprising means for maintaining the position of said at least one support member when said drive means is inoperative.

22. The invention according to claim 21 wherein said drive means comprises a rotatable shaft and wherein said means for maintaining position comprises a compression bearing rotatably supporting said shaft.

23. The invention according to claim 19 and further comprising means for manually displacing said at least one support.

24. The invention according to claim 19 and further comprising means for monitoring the position of said at least one support member and generating a representative control input signal to said electronic controller.

25. The invention according to claim 24 wherein said means for monitoring comprises an encoder.

26. The invention according to claim 19 wherein said at least one support member carries a nut wherein said drive means includes a rotatable threaded shaft for threadably engaging said nut.

27. The invention according to claim 26 wherein said at least one support member is tubular and said shaft and said nut are concentrically confined within said tubular support member.

28. The invention according to claim 24 wherein said controller includes means for storing a representative control input signal at a predetermined position of said at least one support member,
   an actuator for selecting said predetermined position at a first actuation, and actuating said drive means for returning said at least one support member to said predetermined position upon a subsequent actuation of said actuator.

29. The invention as defined in claim 24 wherein said means for monitoring comprises a sensor mechanism substantially shorter than said at least one support member.

30. Apparatus for controlling the pressure of a parenteral liquid container comprising:
   hanging means for supporting said parenteral liquid containers;

telescoping support means for changing the height of said hanger means including a plurality of concentric elongated support members;

drive means for vertically displacing at least one of said concentric support members; and an electronic controller for controlling said drive means including means for automatically actuating said drive means for displacing said at least one support member in a vertically upward direction to increase fluid pressure, and means for automatically displacing said at least one support member in a vertically downward direction to decrease fluid pressure.

* * * * *